United States Patent [19]

Krieser

[11] Patent Number: Plant 5,997

[45] Date of Patent: May 19, 1987

[54] *DRACAENA-DEREMENSIS*-WARNECKEI-SKUNKY

[76] Inventor: Roy J. Krieser, 1931 Herman Rd., Manitowoc, Wis. 54220

[21] Appl. No.: 826,601

[22] Filed: Feb. 6, 1986

Related U.S. Application Data

[63] Continuation of Ser. No. 659,075, Oct. 9, 1984, abandoned.

[51] Int. Cl.[4] ..... A01H 5/00

[52] U.S. Cl. ..... Plt./88

[58] Field of Search ..... Plt./88

*Primary Examiner*—Robert E. Bagwill

*Attorney, Agent, or Firm*—Schwartz, Jeffery, Schwaab, Mack, Blumenthal & Evans

[57] ABSTRACT

A dracaena plant named 'Skunky' particularly characterized by the combined characteristics of a solid white center stripe extending through the leaf and being approximately the width of the green marginal stripes midway of the length of the leaf, an erect and compact growth habit, and by its abundance of regularly spaced leaves which give the plant a bushy appearance.

4 Drawing Figures

This is a continuation application of Ser. No. 659,075, filed Oct. 9, 1984, now abandoned.

The present invention comprises a new and distinctive cultivar of dracaena plant, botanically known as *Dracaena deremensis,* and known by the cultivar name 'Skunky'.

The new cultivar 'Skunky' is a sport of a *Dracaena deremensis* cultivar known by the varietal name 'Warneckei' which was growing in a cultivated area in Manitowoc, Wis. The discovery was made in 1973, and it was observed that a distinctly different and unique leaf variegation appeared in a root shoot of the parent cultivar. The shoot was removed from below the base of the parent cultivar, air-layered and severed. Subsequent asexual propagation performed by me beginning in approximately 1976 by the taking of tip cuttings has demonstrated that the combination of characteristics as disclosed herein for 'Skunky' are firmly fixed and are retained through successive generations of asexual reproduction.

'Skunky' has not been observed under all possible environmental conditions. The phenotype may vary significantly with variations in environment such as temperature, light intensity, and day length. The following observations, measurements and comparisons describe plants grown by me in Manitowoc, Wis. in the home and under greenhouse conditions which approximate those generally used in commercial practice.

The following characteristics have been repeatedly observed and are determined to be basic characteristics of 'Skunky', which in combination distinguish this new dracaena as a new and distinct cultivar.

1. Perhaps the most outstanding feature of 'Skunky' is the purity of the white of the single white stripe centered longitudinally in the leaf. The white stripe extends through the thickness of the leaf, and the purity is visible on the under surface of the leaf as well, including the region of the midrib. This is not true with the parent or other dracaena cultivars in which greening appears at or around the midrib of the under surface of the leaf.

2. The solid white stripe combines with the relatively dark green leaf color to either side thereof to form a very showy variegation. Generally speaking, the solid white stripe in the center of the leaf is approximately one-third the total width of the leaf in approximately the longitudinal midpoint thereof. Near the top of the leaf, the ratio of white is much greater. The proportion will vary somewhat from plant to plant, and will also vary with the age of the plant. Further, as the new plant approaches its blooming stage, the white stripe near the crown of the plant becomes somewhat wider.

3. The new cultivar has a very compact growth habit which makes it appear relatively more bushy than other dracaenas of this species. The appearance of bushiness is enhanced by the frequent appearance of shoots at or near the soil line.

4. Despite its compact growth habit, 'Skunky' grows straight and erect, with its leaves very regularly spaced. The newest leaf normally stands relatively straight at the top of the plant, and the next two or perhaps three leaves tend to bend more perpendicular to the axis of the plant. The remaining leaves arch and recurve more than the leaves of the parent cultivar.

5. Due to its erect yet compact growth habit and pleasing leaf variegation, 'Skunky' makes an excellent house plant or specimen plant for offices, libraries, or similar environments.

6. The new cultivar is easy to propagate from cuttings, with the callus at the cut end forming and rooting quickly.

Of the commercial cultivars known to the present inventor, comparisons can be made with the parent cultivar 'Warneckei', and the cultivars 'Longii' and 'Bausei'.

As opposed to the relatively wide, solid white stripe of the present cultivar, the parent cultivar has green leaves which are streaked with a generally milky or creamy green in the center, bordered by a translucent white band on each side and inside the green edges. The visual differences in leaf color are remarkably apparent. In addition, the parent cultivar has a stronger growth habit and produces a larger plant.

The cultivar 'Longii' is distinguishable from the new cultivar in several respects. Although 'Longii' is reputed to have a solid white center stripe, inspection of the cultivar reveals that there is always a green midrib in the white stripe on the under surface of the leaf, and frequently a green streak or stripe appears on the top of many of the leaves. The ratio of length to width of the leaves of 'Longii' is also different. A typical leaf of 'Longii' is approximately 10–11" long and approximately $1\frac{3}{4}''$ wide, whereas 'Skunky' is approximately $2\frac{1}{4}''$ wide. Further, in the propagation of 'Longii', as reported by others, there is a tendency for the white center stripe to revert to green. This is contrary to 'Skunky' in that in the several years of propagating the new cultivar, no such reversion has ever been observed. A further distinction is that the white stripe of 'Longii' is proportionally less dominant than the white solid stripe of 'Skunky'. The width of the narrow white center stripe of 'Longii' is on the order of 1/7 to $\frac{1}{4}$ of the total width of the leaf, as opposed to the solid white stripe of 'Skunky' which is at least $\frac{1}{3}$ or greater than the total width of the leaf.

The cultivar 'Bausei' is similar in many respects to the parent cultivar 'Warneckei'. 'Bausei' is principally characterized by two white bands near the center of the leaf, always separated by a thin milky green stripe. The visual appearance is clearly distinguishable from the relatively wide solid white stripe of 'Skunky'.

The accompanying photographic drawings show typical growth, leaf form and color characteristics of 'Skunky'.

FIG. 1 shows a single plant of 'Skunky',

FIG. 2 two specimen plants, and

FIGS. 3 and 4 groups of plants of 'Skunky' at various stages of growth.

The colors in the photographic drawings are as true as possible with color illustrations of this type.

Color references stated below are to the Exotica Horticultural Color Guide, published by A. B. Graf, Roehrs Company, East Rutherford, N.J. Although the color value stated below is not precisely depicted in the photograph drawings, the stated color value is the closest to the true color of the marginal green portions of the leaves. The color values were taken in Manitowoc, Wis.

Classification:

*Botanical.*—*Dracaena deremensis* cv. 'Skunky'.

*Commercial.*—Dracaena.

Propagation: By tip cuttings which root quickly and easily.

Plant: Herbaceous.

*Form.*—Compact, yet straight and erect. The leaves are very regularly spaced and tightly grouped. The frequent growth of shoots at or near the soil line enhance the compact, bushy appearance.

*Size.*—Average growth rate, eventually reaching 30" or more in height. The plants shown in FIGS. 1 and 2 are approximately one year old.

*Leaves.*—Size: Mature leaves are 10–11" in length and typically $2\frac{1}{4}''$ or more in width. Shape: Lanceolate, tip acute; center leaf generally erect, next 2–3 leaves semi-erect, and remaining leaves arched and reversed. Color: Solid white stripe in center, and marginal green stripes approximately 68 Pine Green in color. The ratio of the solid white stripe to the total leaf width is approximately 1:3 midway of the length of the leaf, with the ratio of white to green increasing substantially toward and at the acute tip. The ratio of white to green also increases near the crown just prior to blooming.

I claim:

1. A new and distinct cultivar of *Dracaena deremensis* named 'Skunky', as illustrated and described, and particularly characterized by its solid white center stripe extending through the leaf and being approximately the width of the green marginal stripes midway of the length of the leaf, its erect and compact growth habit, and its abundance of regularly spaced leaves which give the plant a bushy appearance.

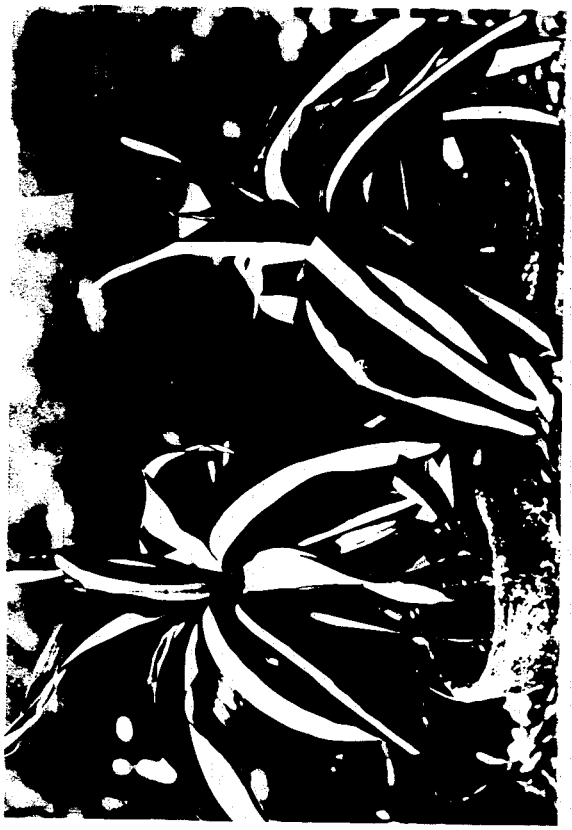
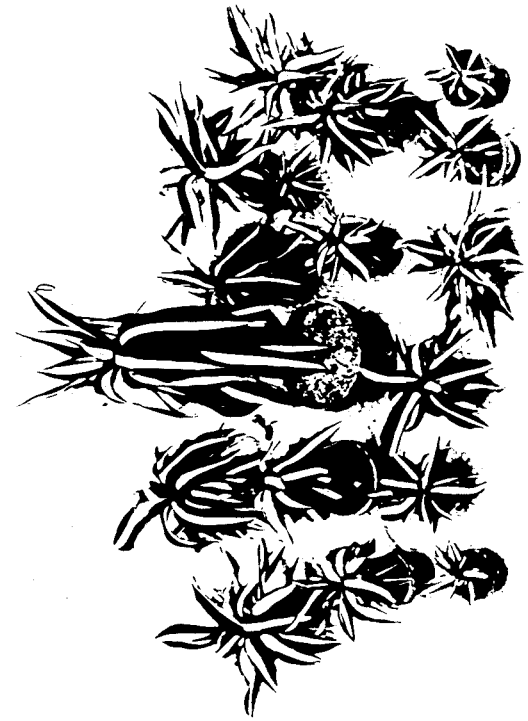
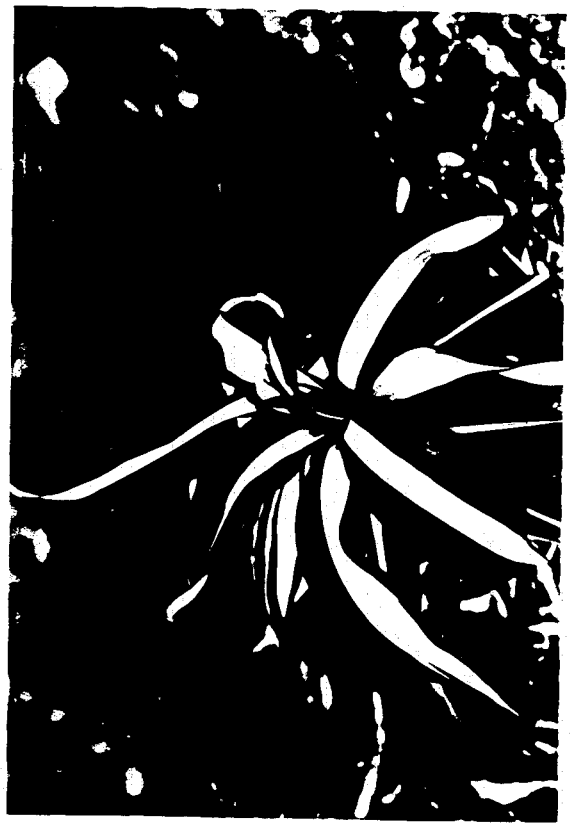
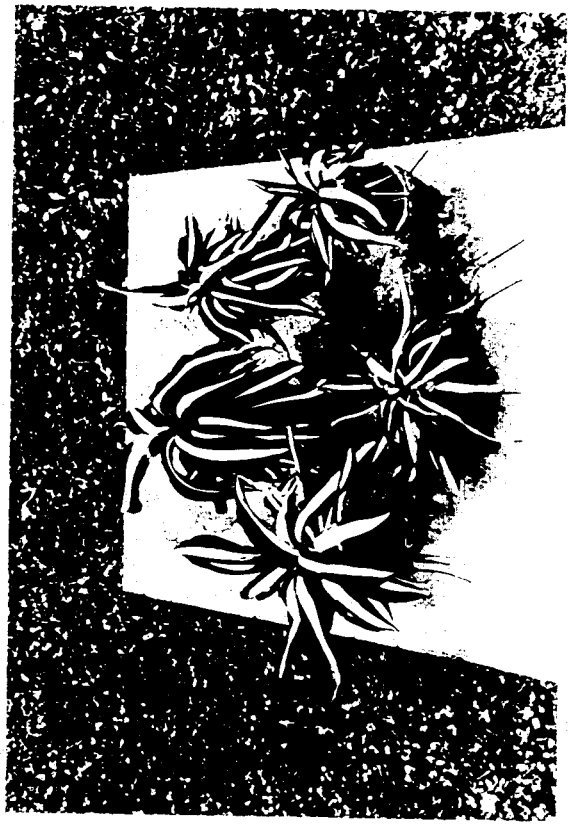

* * * * *